(12) United States Patent
Ting

(10) Patent No.: US 11,234,582 B2
(45) Date of Patent: Feb. 1, 2022

(54) ENDOSCOPE SYSTEM

(71) Applicant: OPCOM INC., New Taipei (TW)

(72) Inventor: Chih-Yu Ting, New Taipei (TW)

(73) Assignee: OPCOM INC., New Taipei (TW)

( * ) Notice: Subject to any disclaimer, the term of this patent is extended or adjusted under 35 U.S.C. 154(b) by 655 days.

(21) Appl. No.: 16/114,196

(22) Filed: Aug. 27, 2018

(65) Prior Publication Data
US 2019/0059703 A1    Feb. 28, 2019

Related U.S. Application Data

(60) Provisional application No. 62/551,299, filed on Aug. 29, 2017.

(51) Int. Cl.
| | |
|---|---|
| *A61B 1/00* | (2006.01) |
| *A61B 1/04* | (2006.01) |
| *A61B 1/05* | (2006.01) |
| *A61B 1/005* | (2006.01) |
| *A61B 1/012* | (2006.01) |
| *A61B 1/01* | (2006.01) |

(52) U.S. Cl.
CPC ........ *A61B 1/00121* (2013.01); *A61B 1/0052* (2013.01); *A61B 1/00059* (2013.01); *A61B 1/00087* (2013.01); *A61B 1/00105* (2013.01); *A61B 1/00124* (2013.01); *A61B 1/01* (2013.01); *A61B 1/0125* (2013.01); *A61B 1/042* (2013.01); *A61B 1/00006* (2013.01); *A61B 1/05* (2013.01)

(58) Field of Classification Search
None
See application file for complete search history.

(56) References Cited

U.S. PATENT DOCUMENTS

| | | | | |
|---|---|---|---|---|
| 8,137,265 | B2 * | 3/2012 | Joko | G02B 23/2484 |
| | | | | 600/118 |
| 8,537,210 | B2 * | 9/2013 | Omori | A61B 1/0638 |
| | | | | 348/68 |
| 8,553,075 | B2 * | 10/2013 | Kubo | A61B 1/063 |
| | | | | 348/65 |
| 8,690,765 | B2 * | 4/2014 | Takasugi | G01N 21/6456 |
| | | | | 600/160 |
| 8,979,741 | B2 * | 3/2015 | Igarashi | A61B 1/0005 |
| | | | | 600/160 |
| 10,034,600 | B2 * | 7/2018 | Igarashi | A61B 5/1459 |
| 2004/0171913 | A1 * | 9/2004 | Saruya | A61B 1/00121 |
| | | | | 600/132 |
| 2004/0215060 | A1 * | 10/2004 | Ueno | A61B 5/0071 |
| | | | | 600/160 |
| 2006/0116550 | A1 * | 6/2006 | Noguchi | A61B 1/00121 |
| | | | | 600/132 |

(Continued)

*Primary Examiner* — Timothy J Neal
*Assistant Examiner* — William B Chou
(74) *Attorney, Agent, or Firm* — Winston Hsu

(57) ABSTRACT

An endoscope system is provided. The endoscope system includes an insert tube and a handle. The insert tube includes a first connector, a first controller, a first parameter and an insert-tube data. The first parameter and the insert-tube data are corresponding to each other. The handle includes a second connector and a second controller. The second connector electronically connects to the first connector, and the second controller receives and accords to the first parameter to generate at least one first control signal to the first controller to control the insert tube.

18 Claims, 4 Drawing Sheets

(56) References Cited

U.S. PATENT DOCUMENTS

| | | | |
|---|---|---|---|
| 2012/0143002 A1* | 6/2012 | Aranyi | A61B 1/00174 600/104 |
| 2014/0142383 A1* | 5/2014 | Blumenzweig | A61B 1/0011 600/110 |
| 2017/0188795 A1* | 7/2017 | Ouyang | A61B 1/00048 |

* cited by examiner

ENDOSCOPE SYSTEM

CROSS REFERENCE TO RELATED APPLICATIONS

This application claims the benefit of U.S. Provisional Application No. 62/551,299, which was filed on Aug. 29, 2017, and is incorporated herein by reference.

BACKGROUND OF THE INVENTION

1. Field of the Invention

The invention relates in general to an endoscope system, and more particularly to the endoscope system which has a plurality of insert tubes with different functions, different appearances, different sizes and different identifications corresponding to each insert tube. A handle of the endoscope system connects and controls one of the insert tubes with its identification.

2. Description of the Prior Art

Currently, an endoscope usually includes an insert tube, a handle and a cable, wherein, the insert tube, the handle and the cable are connected to each other, and the handle and the insert tube are usually fixed and can't be detached from each other. If the endoscope is a reusable endoscope, the elements of the endoscope may be designed as the handle and the insert tube are detached from each other for disinfecting, delivering conveniently or personal hygiene, and before the endoscope is operated, the handle and the insert tube may be assembled with each other.

However, when the handle and the insert tube are assembled with each other, the connectors between the handle and the insert tube may not be connected completely, the image of the endoscope may have the noise or the endoscope may have no images, even the insert tube are separated from the handle easily during use.

Moreover, an endoscope is limited for one part of the patient's body, if the endoscope isn't fitting the patient, the endoscope may be replaced with a new one, or if the patient needs to be observed or operated many parts of the patient's body, the patient may need many endoscopes with different functions for observing or operating the different parts of the patient, but it's may be increasing cost and decreasing the availability of each endoscope.

SUMMARY OF THE INVENTION

The disclosure is directed to an endoscope system. The endoscope system has a plurality of insert tubes, each of them is different to each other and each of them has identification data for identifying, when one of the insert tubes connects to the handle of the endoscope system.

According to one aspect of the present disclosure, an endoscope system is provided. The endoscope system includes an insert tube and a handle. The insert tube includes a first connector, a first controller, a first parameter and an insert-tube data. The first parameter and the insert-tube data are corresponding to each other. The handle includes a second connector and a second controller. The second connector electronically connects to the first connector, and the second controller receives and accords to the first parameter to generate at least one first control signal to the first controller to control the insert tube.

According to another aspect of the present disclosure, an endoscope system is provided. Each insert tube includes a first connector, a first controller, a first parameter and an insert-tube data. The first parameter and the insert-tube data are corresponding to each other. The handle includes a second connector and a second controller. The second connector electronically connects to the first connector of one of the insert tubes, and the second controller receives and accords to the first parameter of the insert tube connecting to the handle to generate at least one first control signal to the first controller to control the insert tube.

By the features described above, the present invention provides an endoscope system, each insert tube provides its own the first parameter to be identified by the handle, when the handle connects one of the insert tubes, the handle accords to the first parameter corresponding to the connected insert tube to look for the insert-tube data corresponding to the connected insert tube to operate and control the function modes of the connected insert tube. The handle connects to one of the insert tubes as necessary for observing the different parts of the patient's body or operating the different surgical operations. The handle and one of the insert tubes may be assembled or detached conveniently in accordance with the first connector and the second connector, and the handle may receive many insert-tube data in a short time to increasing the functionality and the availability of the endoscope system.

These and other objectives of the present invention will no doubt become obvious to those of ordinary skill in the art after reading the following detailed description of the preferred embodiment that is illustrated in the various figures and drawings.

DETAILED DESCRIPTION

Preferred embodiments are disclosed below for elaborating the invention. Various lengths, such as optical focus lengths or distances, of a plurality of micro lenses are applied on a plurality of detecting pixels, such that in an autofocus process, the time consumption can be reduced, and the accuracy can be improved. The following embodiments are for the purpose of elaboration only, not for limiting the scope of protection of the invention. Besides, secondary elements are omitted in the following embodiments to highlight the technical features of the invention.

Figure 1:
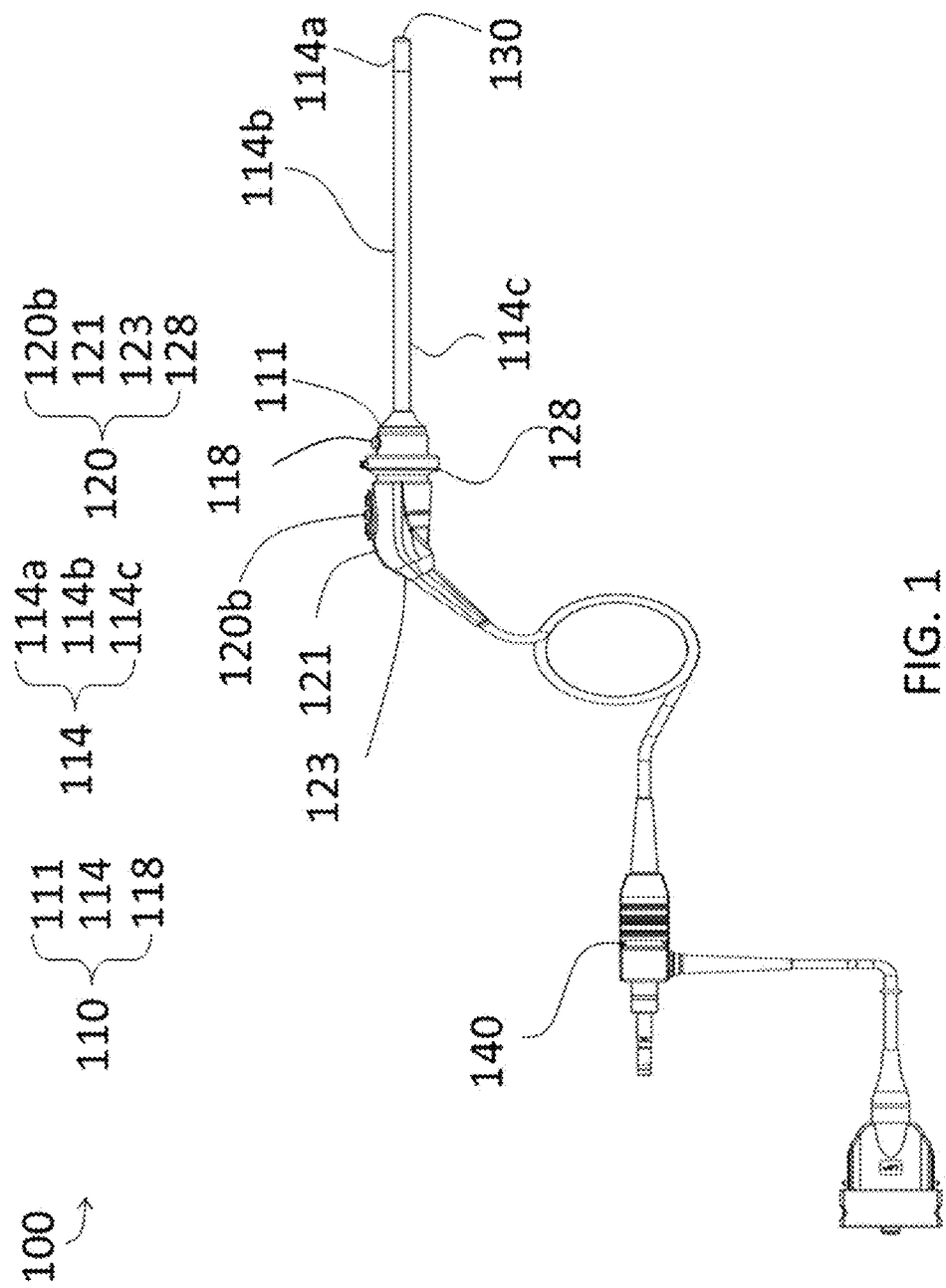
FIG. 1 is a side view schematically showing a whole endoscope system according to one embodiment of the present invention.
Figure 2:
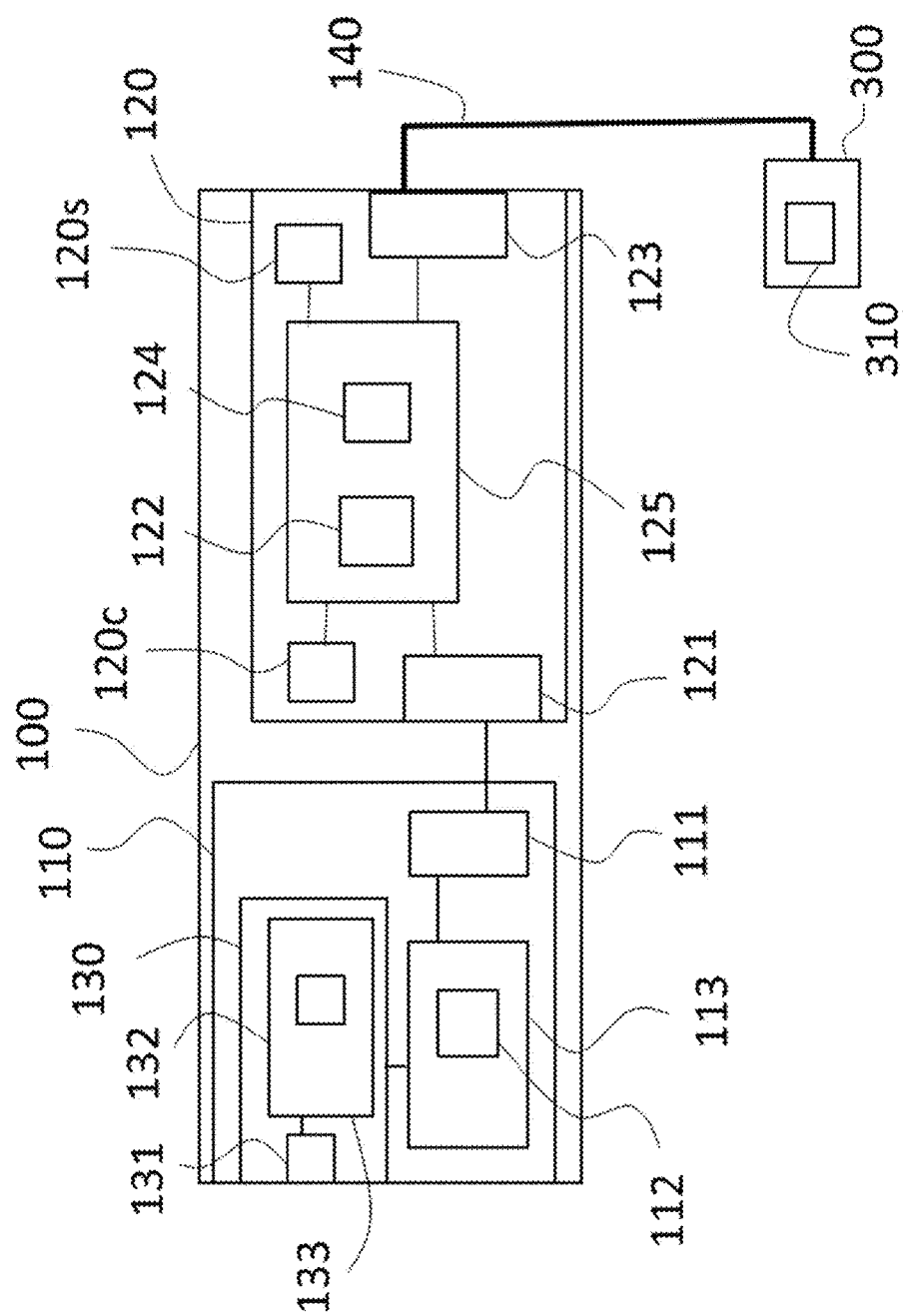
FIG. 2 is a block diagram schematically showing an insert tube which electronically connects to a handle of the endoscope system according to one embodiment of the present invention.
Figure 3:
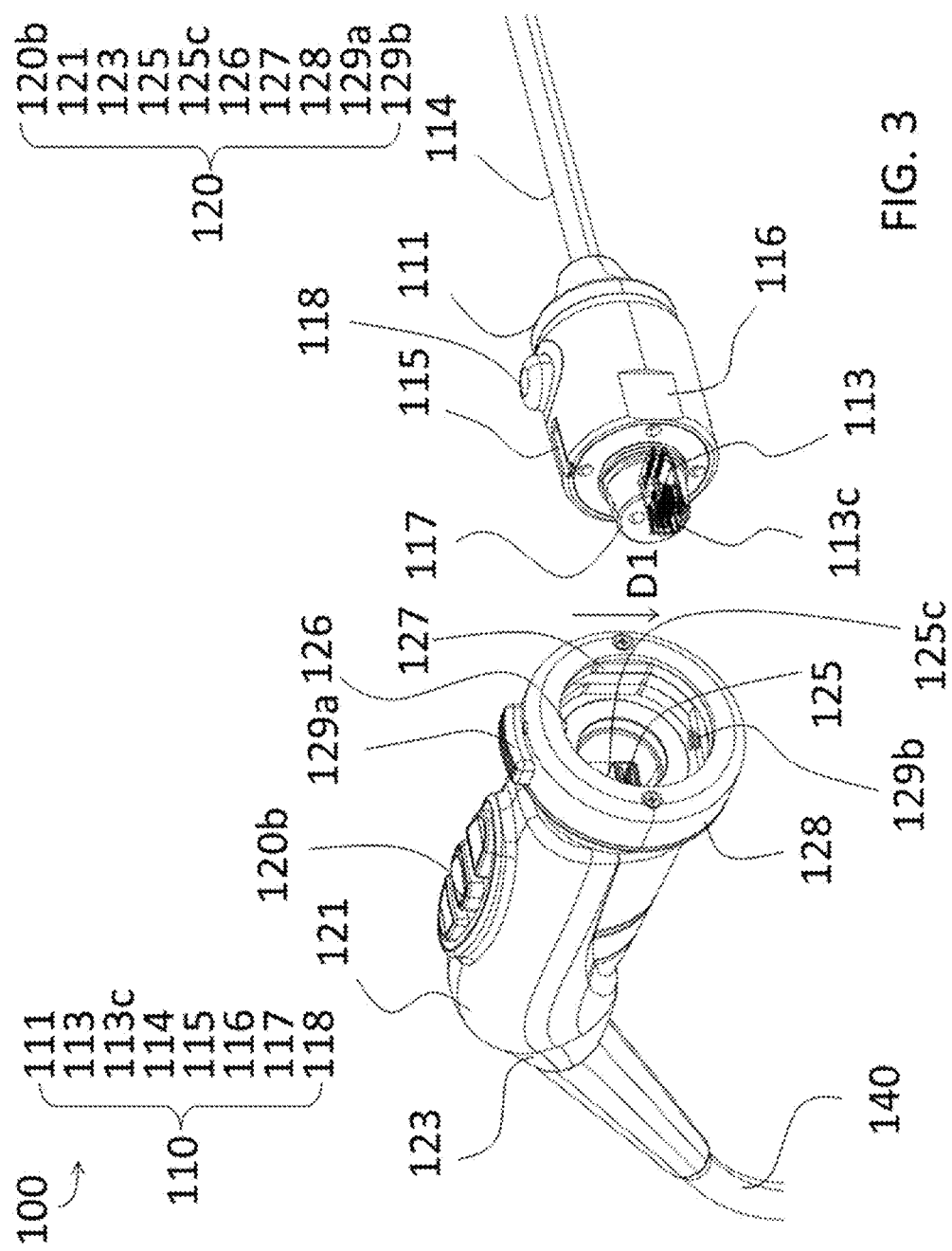
FIG. 3 is a fragmentary enlarged view schematically showing an insert tube and a handle of the endoscope system, and the insert tube and the handle are detached from each other according to one embodiment of the present invention.

Reference is now made to FIG. 1, which is a side view schematically showing a whole endoscope system according to one embodiment of the present invention; FIG. 2, which is a block diagram schematically showing an insert tube which electronically connects to a handle of the endoscope system according to one embodiment of the present invention; and FIG. 3, which is a fragmentary enlarged view schematically showing an insert tube and a handle of the endoscope system, and the insert tube and the handle are detached from each other according to one embodiment of the present invention. As shown in FIG. 1 to FIG. 3, an endoscope system 100 includes at least one insert tube 110 and a handle 120. Here, the endoscope system 100 is exemplified to include an insert tube 110 and a handle 120. One of the handle 120 connects to one end of the insert tube 110. The endoscope system 100 may be a have a disposable endoscope system or a reusable endoscope system, or may have a disposable endoscope or a reusable endoscope. The disposable endoscope or the reusable endoscope may be chosen in accordance with user's needed. The insert tube 110 may be a flexible tube or an inflexible tube. But it is not limit this invention.

In the current embodiment, the insert tube 110 includes a first connector 111, a first controller 112, a first parameter (no shown), an insert-tube data (no shown), a plurality of function modes (no shown) and a second circuit board 113. Wherein, the first parameter and the insert-tube data are corresponding to each other, respectively, and the function modes correspond to the first parameter and the insert-tube data, respectively. Furthermore, the first parameter, the insert-tube data and the function modes may be corresponding to each other.

The insert tube 110 further includes a distal section 114a, a bending section 114b and an extending section 114c, and the distal section 114a, the bending section 114b and the extending section 114c connect with each other to form an insert portion 114. The insert portion 114 connects to one end of the first connector 111. Wherein, the first controller 112 further is disposed in and electronically connects to the second circuit board 113. The second circuit board 113 includes a port 113c. The first controller 112 may be a microcontroller or a microprocessor.

The first connector 111 of the insert tube 110 may be formed from a housing. The first connector 111 further includes a space (no shown). Wherein, the first controller 112 and the second circuit board 113 may further be received in the space of the first connector 111. The insert tube 110 further includes a first fastener 115 and a second fastener 116. The first fastener 115 and the second fastener 116 are disposed on an outer side of the first connector 111, which means a surface of the housing. A first engager 117 is disposed in the other end of the first connector 111, and the first engager 117 may be a protrusion or a concave section. Here, the first engager 117 is exemplified to be a protrusion and disposed in the other end of the first connector 111. The port 113c of the second circuit board 113 is further disposed in the first engager 117 and a part of the port 113c of the second circuit board 113 is exposed from the first engager 117. The first fastener 115 is disposed above the outer side of the first connector 111 and may be a recess, and the second fastener 116 may be determined two first components, such as two concave sections, are disposed on two corresponding sides of the first connector 111, and the second fastener 116 as two first components are different by 180 degrees in position in the circumference direction of the first connector 111. The first fastener 115 and the second fastener 116 are different by 90 degrees in position in the circumference direction of the first connector 111. The first connector 111 of the insert tube 110 of the current embodiment may be a cylinder or a tube. But the present invention is not limited to the embodiments mentioned above.

The endoscope system 100 further includes at least one camera module 130. The camera module 130 includes a camera 131, a sensor 132, a first circuit board 133 and a wire (no shown). Wherein, the circuit board 133, the camera 131, the wire and the sensor 132 electronically connect with each other. The camera 131, the sensor 132 and the first circuit board 133 are further disposed in the distal section 114a of the insert tube 110. The wire is disposed through the bending section 114b and the extending section 114c to the first connector 111, and the wire electronically connects to the second circuit board 113 disposed in the first connector 111 of the insert tub 110.

In the current embodiment, the insert tube 110 further includes at least one first operating portion 118, the first operating portion 118 is disposed in the outer side of the insert tube 110, which means the surface of the first controller 111 of the insert tube 110. The first operating portion 118 may be a button for controlling the camera 131 of the camera module 130 and/or the sensor 132 to switch and perform at least one the function mode. But the present invention is not limited to the embodiments mentioned above.

In the current embodiment, the insert-tube data of the insert tube 110 includes a capture resolution, a field of vision, a range of bending angle, a focus, a length of the insert portion and a count of usage. And the capture resolution, the field of vision, the range of bending angle, the focus, the length of the insert portion and the count of usage correspond to the function modes, respectively. Furthermore, at least one the function mode corresponds to the bending section. Therefore, a frequency of usage and a bending level of the bending section 114b of the insert tube 110 may be obtained in accordance with a range of bending angle and a count of usage of the insert-tube data. At least one the function mode corresponds to the camera module 130. Therefore, a capture resolution, a field of vision and a focus of the camera 131 and the sensor 132 of the camera module 130 may be obtained in accordance with the capture resolution, the field of vision and the focus of the insert-tube data, even the endoscope system 100 accords to the bending level of the bending section 114b to capture meaningful images.

In an alternative embodiment, the handle 120 may further include a storage unit 120s, and the storage unit 120s stores the insert-tube data.

In the current embodiment, the handle 120 includes a second connector 121, a second controller 122, a connecting unit 123, an image processor 124 and a third circuit board 125. Wherein, the second controller 122, the image processer 124, the connecting unit 123 and the third circuit board 125 connect with each other, and the second controller 122 and the image processer 124 are further disposed in the third circuit board 125. The third circuit board 125 includes a port 125c, and the second controller 122 may be a microcontroller or a microprocessor.

The second connector 121 of the handle 120 may be formed from a housing. The second connector 121 further includes a space (no shown). The second controller 122, the connecting unit 123, the image processor 124 and the third circuit board 125 are received in the space of the second connector 121. The handle 120 further includes a third fastener 126, a fourth fastener 127 and a second engager 128. The third fastener 126 and the fourth fastener 127 are disposed in the second connector 121, respectively, which means the third fastener 126 and the fourth fastener 127 are disposed on a surface of the housing, respectively, even are disposed on the second engager 128. The second engager 128 may be a protrusion or a concave section. Here, the second engager 128 is exemplified to be a concave section and disposed in a side of the second connector 121. The port 125c of the third circuit board 125 is further disposed in one end of the second connector 121, which means the port 125c of the third circuit board 125 is disposed on the bottom of the second engager 128 and a part of the port 125c of the third circuit board 125 is exposed from the bottom of the second engager 128. The third fastener 126 and the fourth fastener 127 are further disposed in a side face of the second engager 128, and the third fastener 126 is disposed above the second connector 121, which means on the top inner face of the second engager 128, and third fastener 126 corresponds to the first fastener 115 of the first connector 111 of the insert tube 110. The fourth fastener 127 corresponds to the second fastener 116 of insert tube 110. The third fastener 126 may be a protrusion, and the fourth fastener 127 may be determined two second components, such as two convex faces, and the fourth fastener 127 as two second components are different by 180 degrees in position in the circumference direction of the second connector 121. The third fastener 126 and the fourth fastener 127 are different by 90 degrees in position in the circumference direction of the second connector 121. The second connector 121 of the handle 120 of the current embodiment may be a cylinder or a tube. But the present invention is not limited to the embodiments mentioned above.

The second connector 121 of the handle 120 corresponds to and electronically connects to the first connector 111 of the insert tube 110, in other words, when the handle 120 electronically connects to the insert tube 110, the first engager 117 of the insert tube 110 connects to the second engager 128 of the handle 120 with each other, and the first engager 117 may insert or engage to the second engager 128, such as the protrusion is disposed in the concave section. Meanwhile, the first fastener 115 is engaged to the third fastener 126, and third fastener 126 may be slidely disposed in the first fastener 115, such as a protrusion slidely disposed in the concave sections. The second fastener 116 connects to the fourth fastener 127, such as two protrusions correspond to and connect to the concave sections, respectively. Therefore, the first engager 117 engages to the second engager 128, the first fastener 115 and the third fastener 126 connect and engage to the second fastener 116 and the fourth fastener 127 in accordance with the second connector 121 of the handle 120 connects to the first connector 111 of the insert tube 110, and the handle 120 and the insert tube 110 may be fastened and fixed with other to prevent from disassembling easily.

The insert tube 110 further includes an opening (no shown), and the handle 120 further includes an unlock unit 129a and an elastic unit 129b. The opening corresponds to elastic unit 129b and is disposed in the opposite side of the first fastener 115 of the first connector 111. The unlock unit 129a links with the elastic 129b, furthermore, the unlock unit 129a and the elastic unit 129b may move in a first direction D1 or in the reverse first direction D1 together. Therefore, when the insert tube 110 connects to the handle 120, the first connector 111 is disposed in the second connector 121, and the elastic unit 129b is disposed in the opening to fix with each other, the insert tube 110 and the handle 120 are fixed with each other in accordance with the elastic unit 129b and the opening.

In the current embodiment, when the insert tube 110 and the handle 120 are detached from each other, the unlock unit 129a may be pressed in the first direction D1, meanwhile, the unlock unit 129a linking the elastic unit 129b is relatively movable to the second connector 121 in the reverse first direction D1, and then the elastic unit 129b and the opening are detached from each other, furthermore, the elastic unit 129b shifts with the unlock unit 129a out from the opening in the first direction D1. The first connector 111 of the insert tube 110 moves or shifts out from the second connector 121 of the handle 120 in a second direction D2, and then the insert tube 110 and the handle 120 are detached from each other.

In an alternative embodiment, the first connector 111 of the insert tube 110 connects with the second connector 121 of the handle 120, furthermore, the first connector 111 and the second connector 121 are connected and engaged with each other in accordance with the first engager 117 and the second engager 128. Therefore, the first engager 117 and the second engager 128 of the current embodiment may be a receptacle and a plug, or a protrusion and a concave section for connecting, engaging, fixing or detaching easily. But the present invention is not limited to the embodiments mentioned above.

In the current embodiment, when the handle 120 electronically connects to the insert tube 110, the second connector 121 of the handle 120 electronically connects to the first connector 111 of the insert tube 110, the second controller 122 of the handle 120 receives and accords to the first parameter to generate at least one first control signal to the first controller 112 of the insert tube 110 to control the insert tube 110, furthermore, the second controller 122 generates the first control signal in accordance with the first parameter to the first controller 112 to control and select the function modes. In other words, the second controller 122 selects one of the function modes in accordance with the first control signal. For example, the bending section 114b performs the corresponding function mode in accordance with the first control signal of the second controller 122 of the handle 120. The camera 131 and the sensor 132 perform at least one the corresponding function mode in accordance with the first control signal of the second controller 122 of the handle 120.

Figure 4:
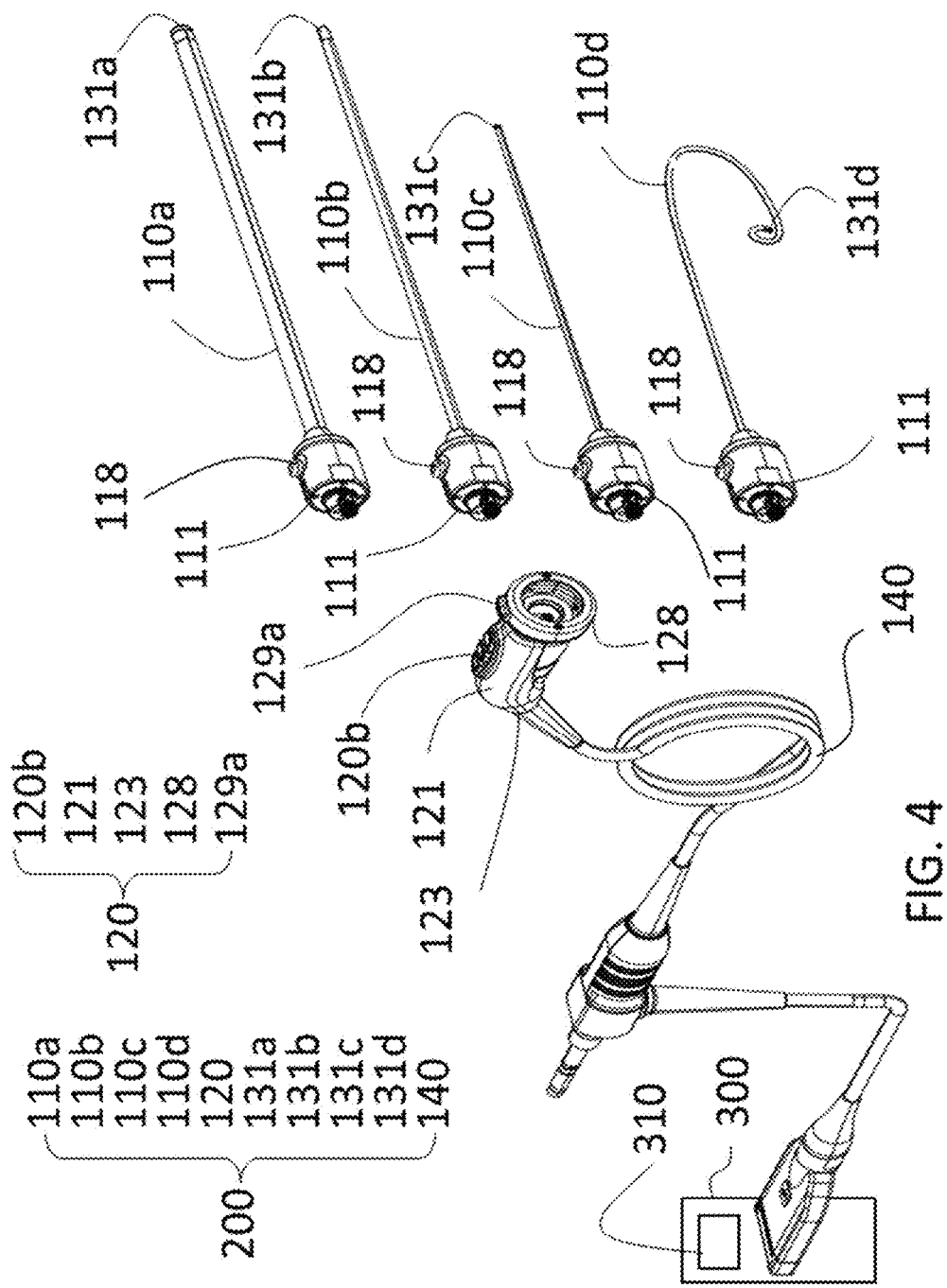
FIG. 4 is a view of an endoscope system, the endoscope system has a plurality of insert tubes and a handle, and the insert tubes have different sizes, different functions and different inner diameter, respectively, according to one embodiment of the present invention.

Reference is now made to FIG. 4, which is a view of an endoscope system, and the endoscope system has a plurality of insert tubes and a handle, the insert tubes have different sizes, different functions and different inner diameter, respectively, according to one embodiment of the present invention. As shown in FIG. 1 to FIG. 4, the endoscope system 200 of the present invention of FIG. 4 is similar to the endoscope system 100 of FIG. 1, and the same element designations and symbols are used in the present embodiment. The difference between the endoscope system 200 of FIG. 4 and the endoscope system 100 of FIG. 1 is that the endoscope system 200 further includes a plurality of the insert tubes 110a, 110b, 110c, 110d and a plurality of camera modules (no shown); and the handle 120 may selectively connect to one of the insert tubes 110a, 110b, 110c, 110d, wherein, a portion of the first parameters of the insert tubes 110a, 110b, 110c, 110d are the same or the first parameters of the insert tubes 110a, 110b, 110c, 110d are different from each other, a portion of the insert-tube data of the insert tubes 110a, 110b, 110c, 110d are the same or the insert-tube data of the insert tubes 110a, 110b, 110c, 110d are different from each other. Furthermore, the insert portions of each insert tube 110a, 110b, 110c, 110d has an inner diameter, the inner diameters of the insert portions of the insert tubes 110a, 110b, 110c, 110d are the same or different from each other, the lengths of the insert tubes 110a, 110b, 110c, 110d are the same or different from each other. The camera modules include a plurality of cameras 131a, 131b, 131c, 131d and a plurality of sensors (no shown), respectively. Each camera 131a, 131b, 131c, 131d has a field of vision, the field of visions of the cameras 131a, 131b, 131c, 131d are the same or different from each other, the sensors of the camera modules are the same or different from each other. But the present invention is not limited to the embodiments mentioned above.

When the handle 120 electronically connects to one of the insert tube 110a, 110b, 110c, 110d, here, the handle 120 is exemplified to electronically connect to the insert tube 110a (no shown). The first controller 112 generates an identification signal (no shown) to the second controller 122, and the second controller 122 receives the identification signal to generate a receiving signal (no shown) in accordance with the identification signal to the first controller 112, the first controller 112 transfers the first parameter to the second controller 122 in accordance with the receiving signal. The second controller 122 of the handle 120 receives and accords to the first parameter of the insert tube, such as the insert tube 110a connecting to the handle 120 to generate at least one first control signal to the first controller 112 to select and control one of the insert tubes, such as the insert tube 110a, to perform at least one the function modes of the insert tube 110a. Furthermore, the second controller 122 of the handle 120 may accord the first parameter of the insert tube 110a to find at least one control method corresponding to the function modes of the insert tube 110a to generate the first control signal and then to control the insert tube 110a.

In the current embodiment, the handle 120 further includes the storage unit 120s, and the storage unit 120 stores the insert-tube data. Therefore, the second controller 122 of the handle 120 looks for the insert-tube data corresponding to the insert tube, such as insert tube 110a from the storage unit 120 in accordance with the first parameter corresponding to the insert tube 110a and then the second controller 122 generates the first control signal to control the insert tube 110a in accordance with the insert-tube data corresponding insert tube 110a. But the present invention is not limited to the embodiments mentioned above.

As shown in FIG. 2, the connecting unit 123 of the handle 120 may transfer at least one the first parameter of the insert tube 110a, 110b, 110c, 110d in accordance with a wireless communication or a wired communication. In another current embodiment, the endoscope system 100, 200 further electronically connects to an external device 300, and the handle 120 transfers the first parameter to the external device 300 in accordance with the connecting unit 123 in the wireless communication or the wired communication. The external device 300 further includes a third controller 310 to generate a third control signal to the second controller 122 of the handle 120 in accordance with the first parameter, the second controller 122 of the handle 120 generates the first control signal to control one of the insert tube 110a, 110b, 110c, 110d to perform the function modes in accordance with the third control signal. The external device 300, for example, a main station or a main system, and the external device 300 includes a monitor.

In an alternative embodiment, when the external device 300 is main system, the endoscope system 100 further includes a cable 140, and the connecting unit 123 of the handle 120 transfers the first parameter in accordance with the wired connection method, two ends of the cable 140 further electronically connect between the external device 300 and the handle 120. The external device 300 and the handle 120 are transferred the insert-tube data and/or the first parameter with each other in accordance with the cable 140, or the images of the camera 131 are transferred to be displayed in the monitor of the external device 300 in accordance with the cable 140. When the connecting unit 123 transfers the first parameter in accordance with the wire, the connecting unit 123 and the external device 300 have a wireless transmitter and receiver module, respectively, and the connecting unit 123 directly connects to the external device 300 or the connecting unit 123 and the external device 300 are transferred the insert-tube data and/or the first parameter in accordance with the wireless transmitter and receiver modules. But the present invention is not limited to the embodiments mentioned above.

In another alternative embodiment, when the external device 300 connects to the handles 120 in accordance with the wireless communication (no shown), the external device 300 electronically connects to the connecting unit 123 of the handle 120, and the external device 300 may be fixed to the connecting unit 123 of the handle 120 by way of insertion. In the current embodiment, the connecting unit 123 and the external device 300 may further be a plug and a socket, and the external device 300 inserts to the connecting unit 123 for connecting the handle 120 to display or transfer the insert-tube data, the first parameter and/or data.

In another alternative embodiment, the handle 120 further includes a second operating portion 120c, and the second operating portion 120c is disposed in the outer side of the handle 120, which means the surface of the handle 120. The second operating portion 120c is further disposed on the outer side of the second connector 121. The second operating portion 120c may be at least one button, and the second operating portion 120c further electronically connects to the second controller 122. The user may further perform the function modes of the insert tube, such as insert tube 110, 110a, in accordance with operating the second operating portion 120c.

The handle 120 selectively connects to one of the insert tubes 110, 110a, 110b, 110c, 110d, wherein, the sizes, the lengths and/or the functions of the insert tubes 110, 110a, 110b, 110c, 110d are different from each other. Each insert tube 110, 110a, 110b, 110c, 110d has its own the first parameter, such as identification data, therefore, when the handle 120 connects to one of the insert tube, such as the insert tube 110a, the handle 120 may generate at least one the first control signal to control at least one the function modes in accordance with the first parameter of the insert tube 110a without inputting any product number, order number or serial number by the user. The handle 120 and the insert tubes 110, 110a, 110b, 110c, 110d are connected with each other in accordance with the first connector 111 and the second connector 121, and the handle 120 and the insert tubes 110, 110a, 110b, 110c, 110d not only are connected firmly, but also are detached from each other conveniently for increasing the functionality of the endoscope system 100, 200 and increasing the availability of the insert tubes 110, 110a, 110b, 110c, 110d and saving the cost.

To summarize, each insert tube 110, 110a, 110b, 110c, 110d provides its own the first parameter to be identified by the handle 120, when the handle 120 connects one of the insert tubes 110, 110a, 110b, 110c, 110d, the handle 120 accords to the first parameter corresponding to the connected insert tube 110, 110a, 110b, 110c, 110d to look for the insert-tube data corresponding to the connected insert tube 110, 110a, 110b, 110c, 110d to operate and control the function modes of the connected insert tube 110, 110a, 110b, 110c, 110d. The handle 120 connects to one of the insert tubes 110, 110a, 110b, 110c, 110d as necessary for observing the different parts of the patient's body or operating the different surgical operations. The handle 120 and one of the insert tubes 110, 110a, 110b, 110c, 110d may be assembled or detached conveniently in accordance with the first connector 111 and the second connector 121, and the handle 120 may receive many insert-tube data in a short time to increasing the functionality and the availability of the endoscope system 100, 200.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An endoscope system comprising:
   an insert tube comprising a first connector, a first controller, a first parameter, an insert-tube data, and a plurality of function modes corresponding to the first parameter and the insert-tube data, the first parameter and the insert-tube data being corresponding to each other; and
   a handle comprising a second connector and a second controller, the second connector electronically connecting to the first connector, the second controller receiving the first parameter to generate at least one first control signal to the first controller and selecting one of the plurality of function modes in accordance with the at least one first control signal to control the insert tube.

2. The endoscope system of claim 1, wherein the insert tube further comprises a distal section, a bending section and an extending section, the distal section, the bending section and the extending section connect with each other to form an insert portion, the insert portion connects to the first connector, at least one the function mode corresponds to the bending section, and the bending section performs the corresponding function mode in accordance with the first control signal of the second controller.

3. The endoscope system of claim 2, wherein the endoscope system further comprises a plurality of the insert tubes, the insert portions of each insert tube have an inner diameter, the inner diameters of the insert portions of the insert tubes are the same or different from each other, and the lengths of the insert tubes are the same or different from each other.

4. The endoscope system of claim 1, wherein the endoscope system further comprises a camera module comprising a camera and a sensor, the insert tube comprises a distal section, the camera module is disposed in the distal section, at least one the function mode corresponds to the camera module, and the camera and the sensor perform the corresponding function mode in accordance with the first control signal of the second controller.

5. The endoscope system of claim 4, wherein the endoscope system further comprises a plurality of the insert tubes, each camera has a field of vision, the field of visions of the cameras are the same or different from each other, and the sensors of the camera modules are the same or different from each other.

6. The endoscope system of claim 1, wherein the insert-tube data comprises a capture resolution, a field of vision, a range of bending angle, a focus, a length of the insert portion and a count of usage, and the capture resolution, the field of vision, the range of bending angle, the focus, the length of the insert portion and the count of usage correspond to the function modes, respectively.

7. The endoscope system of claim 1, wherein the endoscope system further comprises a plurality of the insert tubes, the handle selectively connects to one of the insert tubes, a portion of the first parameters of the insert tubes are the same or the first parameters of the insert tubes are different from each other, and a portion of the insert-tube data of the insert tubes are the same or the insert-tube data of the insert tubes are different from each other.

8. The endoscope system of claim 1, wherein the handle comprises a storage unit, and the storage unit stores the insert-tube data.

9. The endoscope system of claim 1, wherein when the handle electronically connects to the insert tube, the first controller generates an identification signal, and the second controller generates a receiving signal in accordance with the identification signal and the first controller transfers the first parameter to the second controller in accordance with the receiving signal.

10. The endoscope system of claim 1, wherein the endoscope system further comprises a connecting unit, the handle transfers the first parameter to an external device in accordance with the connecting unit, the external device generates a third control signal to the second controller, and the second controller generates the first control signal in accordance with the third control signal.

11. An endoscope system comprising:
    a plurality of insert tube, each insert tube comprising a first connector, a first controller, a first parameter, an insert-tube data, and a plurality of function modes corresponding to the first parameter and the insert-tube data, the first parameter and the insert-tube data being corresponding to each other; and
    a handle comprising a second connector and a second controller, the second connector electronically connecting to the first connector of one of the insert tubes, the second controller receiving the first parameter of the insert tube connecting to the handle to generate at least one first control signal to the first controller and selecting one of the plurality of function modes in accordance with the at least one first control signal to control the insert tube.

12. The endoscope system of claim 11, wherein the insert tube further comprises a distal section, a bending section, and a extending section, the distal section, the bending section and the extending section connect with each other to form an insert portion, the insert portion connects to the first connector, at least one the function mode corresponds to the bending section, and the bending section performs the corresponding function mode in accordance with the first control signal of the second controller.

13. The endoscope system of claim 12, wherein the insert portions of each insert tube have an inner diameter, the inner diameters of the insert portions of the insert tubes are the same or different from each other, and the lengths of the insert tubes are the same or different from each other.

14. The endoscope system of claim 11, wherein the endoscope system further comprises a plurality of camera modules comprising a camera and a sensor, respectively, the insert tube comprises a distal section, the camera modules are disposed in the distal sections, respectively, one of the function modes corresponds to the camera module, and the camera and the sensor disposed in the distal section of the insert tube connecting to the handle perform the function modes in accordance with the first control signal of the second controller.

15. The endoscope system of claim 14, wherein the camera of each camera module has a field of vision, the field of visions of the cameras of camera modules are the same or different from each other, and the sensors of the camera modules are the same or different from each other.

16. The endoscope system of claim 11, wherein a portion of the first parameters of the insert tubes are the same or the first parameters of the insert tubes are different from each other, and a portion of the insert-tube data of the insert tubes are the same or the insert-tube data of the insert tubes are different from each other.

17. An endoscope system comprising:
 an insert tube comprising an opening, a first connector, a first controller, a first parameter and an insert-tube data, the first parameter and the insert-tube data being corresponding to each other; and
 a handle comprising an unlock unit, an elastic unit, a second connector and a second controller, the second connector electronically connecting to the first connector, the second controller receiving the first parameter to generate at least one first control signal to the first controller to control the insert tube, the opening corresponding to the elastic unit and being disposed in the first connector, the unlock unit and the elastic unit linking with each other;
 wherein when the insert tube connects to the handle, the first connector is disposed in the second connector, and the elastic unit is disposed in the opening to fix with each other, the insert tube and the handle are fixed with each other in accordance with the elastic unit and the opening;
 wherein the unlock unit is pressed to link the elastic unit to be detached from the opening for making the first connector of the insert tube detachable from the second connector of the handle.

18. The endoscope system of claim 17, wherein the insert tube further comprises a first fastener and a second fastener, the first fastener and the second fastener are disposed on an outer side of the first connector, the handle further comprises a third fastener and a fourth fastener, and the third fastener and the fourth fastener are disposed in the second connector; when the handle electronically connects to the insert tube, the third fastener is slidably disposed in the first fastener and the second fastener connects to the fourth fastener, so as to fasten the handle with the insert tube.

* * * * *